United States Patent [19]
Brugger et al.

[11] Patent Number: 6,003,556
[45] Date of Patent: Dec. 21, 1999

[54] HINGED CAP FLUID CONNECTOR

[75] Inventors: James M. Brugger, Newburyport, Mass.; Helmut W. Frey, Williamsburg, Va.

[73] Assignee: COBE Laboratories, Inc., Lakewood, Colo.

[21] Appl. No.: 08/725,850

[22] Filed: Oct. 4, 1996

Related U.S. Application Data

[60] Provisional application No. 60/004,895, Oct. 6, 1995.

[51] Int. Cl.$^6$ ........................................ F16L 55/11
[52] U.S. Cl. ......................... 138/89; 138/96 R; 604/263
[58] Field of Search ................... 138/89, 89.4, 96 R, 138/89.1, 89.2, 89.3; 604/263; 215/306, 320, 355; 220/375

[56] References Cited

U.S. PATENT DOCUMENTS

| | | | |
|---|---|---|---|
| 2,705,955 | 4/1955 | Nesset et al. | 138/89 |
| 3,058,472 | 10/1962 | Thornton, Jr. | 138/89 |
| 3,633,586 | 1/1972 | Sheridan | 138/89 |
| 3,741,217 | 6/1973 | Ciarico | 138/89 |
| 4,417,890 | 11/1983 | Dennehey et al. | 138/89 |
| 4,674,640 | 6/1987 | Asa et al. | 215/306 |
| 5,036,889 | 8/1991 | Pherigo | 138/89 |
| 5,041,215 | 8/1991 | Chamberlain, Jr. et al. | 210/136 |
| 5,385,372 | 1/1995 | Utterberg | 285/332 |
| 5,417,247 | 5/1995 | Tarui et al. | 138/89.4 |

*Primary Examiner*—James F. Hook
*Attorney, Agent, or Firm*—Bruce R. Winsor; Mary K. G. Hehman

[57] ABSTRACT

A capped connector for a tubing set and/or medical equipment is provided. The connector comprises a hollow tube having a cap securing leash pivotally attached to its exterior. A cap is pivotally attached to the leash's opposing end. The leash is designed to hold the cap in an orientation that facilitates automated capping while allowing the cap and leash to be rotated away from the connector opening when the cap is not is use.

22 Claims, 6 Drawing Sheets

HINGED CAP FLUID CONNECTOR

RELATED APPLICATIONS

This application is a continuation of co-pending provisional U.S. patent application Ser. No. 60/004,895 filed Oct. 6, 1995.

FIELD OF INVENTION

The present invention relates to capped fluid connectors, and more particularly to improved caps for luer fluid connectors used during dialysis unit priming and waste handling.

BACKGROUND OF THE INVENTION

Luer lock fluid connectors are well known and often preferred for connecting tubing and medical equipment during many medical procedures. Capped fluid connectors are particularly preferred for many medical procedures, such as dialysis procedures, because they allow the sterility of the system to be maintained by the cap when the capped connector end is not attached to another piece of tubing or equipment. For instance, with the WHO® waste handling option for the CENTRY®3 dialysis apparatus manufactured by COBE® Laboratories, Inc., Lakewood, Colo., described in U.S. patent application Ser. No. 5,041,215 to Chamberlain, et al., capped fluid connectors are used with tubing sets for the dialysis unit. During set-up of the dialysis unit, the connector remains capped to maintain the sterility of the extracorporeal system. While the dialysis unit is expelling waste or being primed, the cap may be removed and the connector may be attached to the waste handling option or to a bag of sterile saline solution. Where the connector is capped with a breather cap, the cap may not have to be removed during priming or waste expelling. Of course, capped fluid connectors have many uses in medical treatment in addition to the described example.

It is often preferred for the manufacturer to pre-sterilize capped fluid connectors and ship the sterilized capped fluid connectors to the medical care provider for immediate use. Caps, therefore, should be applied to the connectors prior to sterilization. Manually capping fluid connectors prior to sterilization is labor intensive and, therefore, costly. It is less costly to apply the caps automatically, preferably in the same machine that manufactures the connector with a tethered cap.

Capped connectors are often manufactured by injection molding with separate caps attached to the connector by a flexible tether. In some prior art capped fluid connectors, the tether that attaches the cap to the connector is a flexible cord or leash. This design allows the cap to move in any direction and, therefore, does not facilitate automated capping. It is therefore, desirable to provide a capped luer fluid connector that is capable of being capped automatically, preferably in an injection molding machine.

Prior art capped fluid connectors may also have separate caps which may be automatically capped. Separate caps, however, are more expensive to manufacture because they require a separate mold. Furthermore, separate caps are easily lost when they are removed from the fluid connector.

Prior art capped fluid connectors are also available as a single piece having the cap hinged to an upper edge of the fluid connector. This design allows automated capping, however, it may not allow a threaded sleeve, some caps or the like to mate with the fluid connector because the hinge blocks the threaded sleeve or cap from engaging the corresponding threads on the exterior of the fluid connector.

U.S. Pat. No. 5,385,372 (1995) to Utterberg discloses a capped fluid connector where a rigid side arm maintains a hinged cap at a fixed distance from the connector's open end. The design of the Utterberg hinged cap requires that the rigid side arm hold the cap a fixed distance from the side of the connector, to allow sufficient space for the cap to cover the connector's open end. The rigid side arm is not movable and, therefore, maintains a constant space between the rigid side arm and connector wall. Therefore, the side arm cannot be moved out of the way when the connector is open and the cap is not being used. This design may not be compatible for use with various pieces of medical equipment, such as the WHO® waste handling option mentioned above, where the rigid side arm configuration would hinder or block attachment of the connector to the medical equipment. Further, because the cap is maintained rigidly in close proximity to the connector, there is the risk of manually contaminating the connector when the cap is manipulated.

It is desirable, therefore, to provide a capped fluid connector that may be molded as a single integral piece as well as capped automatically by the same injection molding machine. It is also desirable to provide a selectively rigid cap tether that holds the cap in a fixed position during automated capping but may be released to allow the cap and the tether to be moved out of the way when the connector is open and the cap is not being used. It is also desirable to provide a capped fluid connector that reduces the risk of accidental manual contamination. Against this background, the present invention was developed.

SUMMARY OF THE INVENTION

An important aspect of the present invention is a luer lock fluid connector having a cap and tether injection molded as one integral piece.

Another important aspect of the present invention is a capped luer lock fluid connector capable of being automatically capped.

Another important aspect of the present invention is a capped fluid connector that may be molded as well as capped automatically by the same injection molding machine.

Another important aspect of the present invention is a luer lock connector having a cap tether that holds the cap in a fixed orientation during automated capping while also allowing the cap tether and cap to be moved away from the connector's upper end as desired.

In accordance with these aspects, the present invention comprises a hollow cylindrical connector body having upper and lower open ends. Both connector ends may comprise female luer tapered surfaces and locking protrusions or threads for connecting to tubing or equipment at either end. A cap tether is fixed to the connector's external wall proximate to the connector's upper open end. The cap tether may be pivotally fixed to the connector by a living hinge at its first end and to a cap by a living hinge at its second end. The cap may comprise a breather cap and locking hook for engaging a locking lip fixed to the connector's upper end. The connector may also comprise a plurality of annular sealing fins and a seating fin proximate to its upper open end.

In a first preferred embodiment, a connecting rib releasably attaches the cap tether to the connector's exterior wall during manufacture and automated capping. Two web like protrusions reinforce the connecting rib during manufacture to prevent it from breaking prematurely. After manufacture, the connecting rib is easily broken under pressure allowing the cap and cap tether to pivot away from the connector body. In a second preferred embodiment, a connecting rib releasably attaches the cap tether to the outer edge of the connector body's upper end. A single web like protrusion, disposed below the connecting rib, reinforces the connecting rib.

A third preferred embodiment also comprises a connecting rib reinforced during manufacture by two web-like protrusions. The connecting rib is easily broken under pressure allowing the cap and cap tether to pivot in a direction perpendicular to the connector body's longitudinal axis: thus, moving the cap tether and cap away from the connector's upper end.

In a fourth embodiment, the cap tether is substantially rigid, and is attached to the connector's uppermost annular positioning flange by a living hinge. A pivot stop is molded to the cap tether's inner surface. During automated capping the cap tether is pivoted towards the connector body until the pivot stop contacts the connector body. When the pivot stop contacts the connector body, the cap tether holds the hinged cap in the proper orientation for automated capping. The cap and cap tether may be pivoted away from the connector body as desired. Alternatively, the entire capped end of the connector may be disposed inside a piece of equipment, allowing fluid to exit the connector through the breather channels of the breather cap.

A fifth preferred embodiment is substantially similar to the fourth embodiment except that the pivot stop is triangular in shape and is fixed to the bottom of the cap tether on its inner surface. During automated capping, the cap tether is rotated towards the connector body until the triangular pivot stop encounters the upper surface of the annular positioning flange. Upon contacting the upper surface of the positioning flange, the rigid cap tether holds the hinged cap in the proper orientation for capping. Alternatively, the entire capped end of the connector may be disposed inside a piece of equipment, allowing fluid to exit the connector through the breather channels of the breather cap.

A sixth preferred embodiment comprises a breather cap attached directly to the outer most edge of the connector's upper end by a living hinge. The top of the cap comprises threads. When the connector engages a threaded sleeve, the cap may be placed in a position parallel to the connector's longitudinal axis, thereby allowing the cap threads to engage the corresponding sleeve grooves. Alternatively, the entire capped end of the connector may be disposed inside a piece of equipment, allowing fluid to exit the connector through the breather channels of the breather cap.

Other objects of this invention will appear from the following description and appended claims, reference being had to the accompanying drawings forming a part of this specification wherein like reference characters designate corresponding parts in the several views.

DETAILED DESCRIPTION OF THE PREFERRED EMBODIMENT

Figure 1:
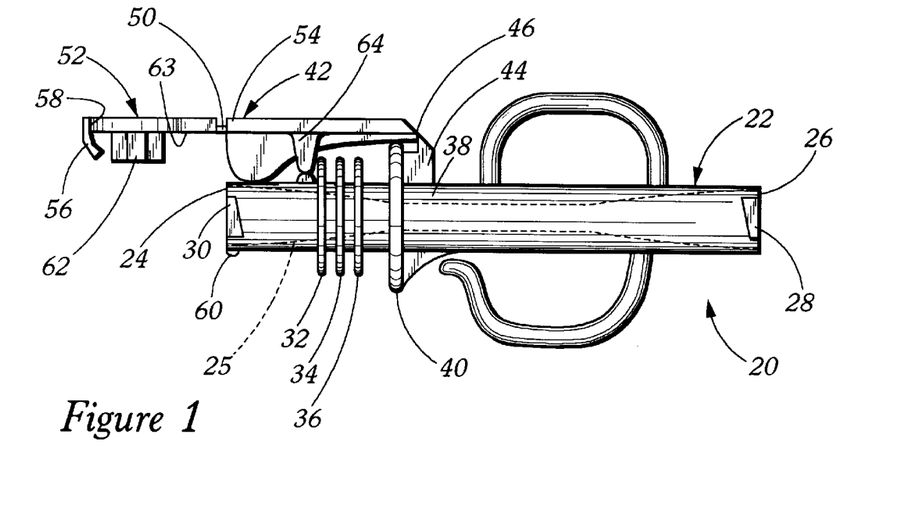
FIG. 1 is a side view of a first preferred embodiment of the present invention showing the cap tether releasably attached to the connector's exterior wall by a breakable connecting rib and the cap in an open position.
Figure 2:
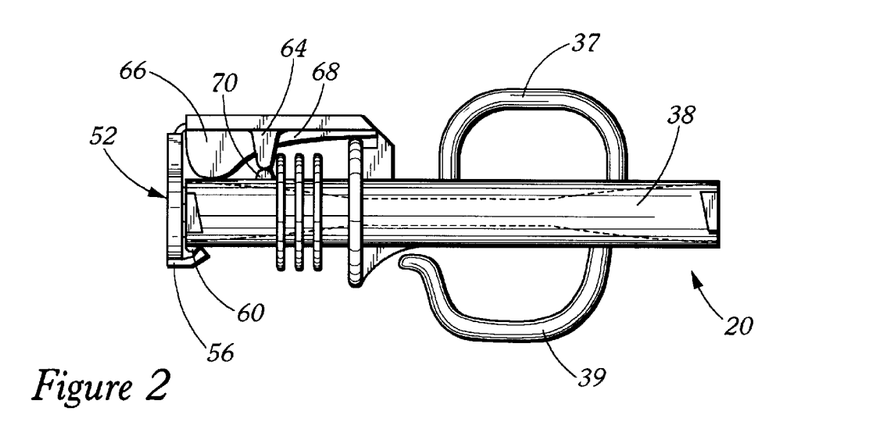
FIG. 2 is a side view of the first preferred embodiment of the present invention showing the cap in the closed position over the connector's upper open end.
Figure 3:
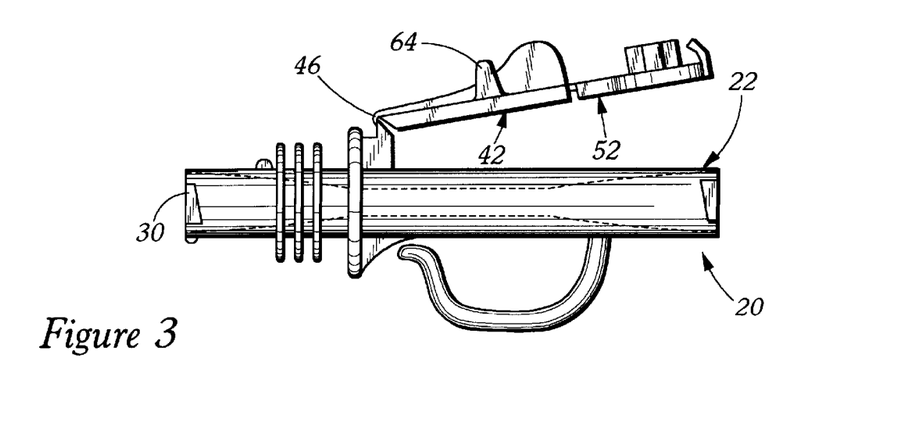
FIG. 3 is a side view of the first preferred embodiment of the present invention showing the cap tether detached from the connector's exterior wall.

Referring first to FIGS. 1 through 3, a first preferred embodiment 20 of the present invention is shown. The first preferred embodiment 20 comprises a hollow tubular connector body 22 having an upper open end 24 and a lower open end 26. Both the upper and lower open ends 24, 26 may comprise a female luer tapered surface 25 for receiving male luer tapered surfaces (not shown). Alternatively, the lower opened end may comprise a male luer tapered surface or any of several well known tubing connections for medical tubing. The upper and lower open ends 24, 26 may also comprise outwardly extending projections or threads 28, 30 for engaging the threads and grooves of a reinforcing outer sleeve carried on the male luer connector (not shown) or the like.

Three sealing fins 32, 34, 36 may be molded to the exterior wall 38 of the connector body 22 proximate to its upper open end 24. A seating fin 40 may be disposed below the sealing fins 32, 34, 36. The seating fin 40 is larger in circumference than the sealing fins 32, 34, 36. These fins 32, 34, 36, 40 may act to position and seal the connector 20 in a piece of medical equipment, tubing or the like. The connector 20 may also comprise a loop 37 disposed below the seating fin 40 for attaching the connector to various pieces of medical equipment, such as extracorporeal tubing sets, I.V. poles, etc. The connector 20 may also comprise a clip 39 for positioning the connector on equipment such as buckets, basins, etc.

A cap tether 42 may be molded to the connector's exterior wall 38 and concurrently to the seating fin 40 at the tether's first end 44. The cap tether 42 may be substantially rigid. A hinge 46 may be molded at the cap tether's first end 44 to allow the tether to rotate towards or away from the connector body 22. A second hinge 50 attaches the cap 52 to the cap tether's second end 54. The second hinge 50 allows the cap 52 to be rotated from the opened to closed position (shown in FIG. 2) and vice versa. It is preferred that the hinges 46, 50 comprise living hinges. As is well known in the art, living hinges comprise thin flexible regions that bend repeatedly without breaking. The living hinges 46, 50 render the rigid tether 42 functionally flexible.

The cap 52 may comprise a hook 56 fixed to its outer annular edge 58. The hook 56 extends below the cap 52 to engage a locking lip 60 when the cap is in the closed position, as best seen in FIG. 2. The cap 52 may be a breather cap having an "X" shaped set of ribs 62 protruding from the cap's bottom surface 63. As is well known in the prior art, the ribs 62 create channels that allow fluids to enter and escape from the connector 20. The cap 52 may also comprise a sealing cap.

The cap tether 42 may be held parallel to the connector body 22 by a breakable connecting rib 64. The cap tether 42, when attached to the connector body 22 the following text—preferably by such a connect rib 64, holds the hinged cap 52 in a functionally rigid orientation that facilitates automated capping. For instance, the cap 52 may thus be held parallel to the connector body 22 allowing an injection molding machine's roller to rotate the cap 52 to the closed position prior to ejecting the connector 20 from the machine.

The connecting rib 64 is reinforced by two web-like protrusions 66, 68. The connecting rib 64 comprises an un-reinforced point 70 that is substantially thinner than the remainder of the connecting rib 64 and not reinforced by the web-like protrusions 66, 68. The un-reinforced point 70 must be sufficiently thin to break easily when an operator moves the cap 52 and the cap tether 42 away from the connector's exterior wall 38 or when pressure is exerted on the first web-like protrusion 66. Such pressure may be exerted by a threaded sleeve, cap or the like. Once broken, the connecting rib 64 easily separates from the connector body's exterior wall 38 and the cap 52 and cap tether 42 become functionally flexible and may pivot freely away from the connector body 22, as best seen in FIG. 3.

The first web-like protrusion 66 may extend toward the connector body wall by a distance sufficient to allow pressure to be exerted on the web-like protrusion 66 when a mating set of threads and grooves engages the connector's locking protrusion or thread 30; thus, the cap tether 42 is automatically separated from the connector's exterior wall 38 when a reinforcing sleeve or fitting engages the locking protrusion or thread 30. The connecting rib 64, may also be broken when the cap 52 and/or cap tether 42 is pulled away from the connector body 22 by an operator.

The entire connector 20 may be injection molded in a single shot. It is desirable that the connector 20 be molded from the polymer suitable for use as a living hinge, such as a medical grade polymer that will withstand a high level of strain without breaking. The present invention may be molded from polyethylene, polypropylene, polyvinyl chloride and other flexible polymers known in the art. The web-like protrusions 66, 68 may be molded to a sufficient size to reinforce the connecting rib 64 during manufacture, thereby preventing the connecting rib 64 from prematurely breaking during injection molding.

Figure 4:
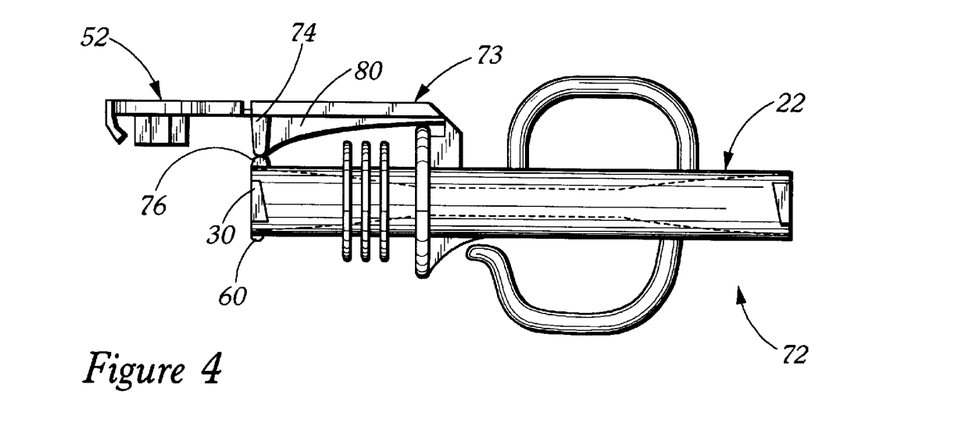
FIG. 4 is a side view of a second preferred embodiment of the present invention showing the cap tether releasably attached to the upper outer edge of the connector's exterior wall and the connector cap in the open position.

Referring next to FIG. 4, a second preferred embodiment 72 of the present invention is shown. The second preferred embodiment 72 is substantially similar to the first preferred embodiment 20, described above, except that the connecting rib 74 is fixed adjacent the very upper outer edge 76 of the connector body 22. The connecting rib 74, therefore, only has one reinforcing web-like protrusion 80 positioned below the connecting rib 74. The connecting rib 74 holds the cap tether 73 in a functionally rigid fixed position, thereby properly orienting the hinged cap 52 for automated capping. When a threaded sleeve of a mating luer lock engages the connector's locking protrusion or thread 30, the threaded sleeve exerts pressure on the connecting rib 74; thus breaking the connecting rib 74 and allowing the cap tether 73 to become functionally flexible and pivot away from the connector body 22. The cap 52 and cap tether 73 may also be rotated away from the connector body 22 when an operator breaks the connecting rib 74 by pulling the cap 52 and cap tether 73 away from the connector 72.

Figure 5:
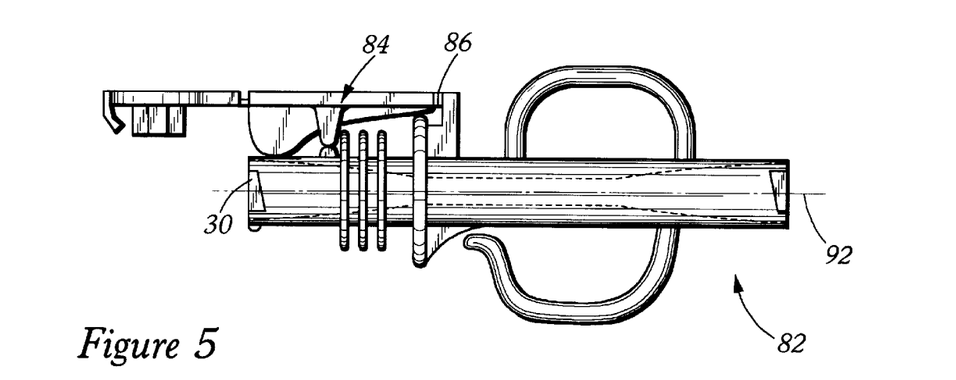
FIG. 5 is a side view of the third preferred embodiment of the present invention showing the cap tether running parallel with the connector body and having a living hinge that allows the cap tether to be rotated perpendicular to the connector's longitudinal axis.
Figure 6:
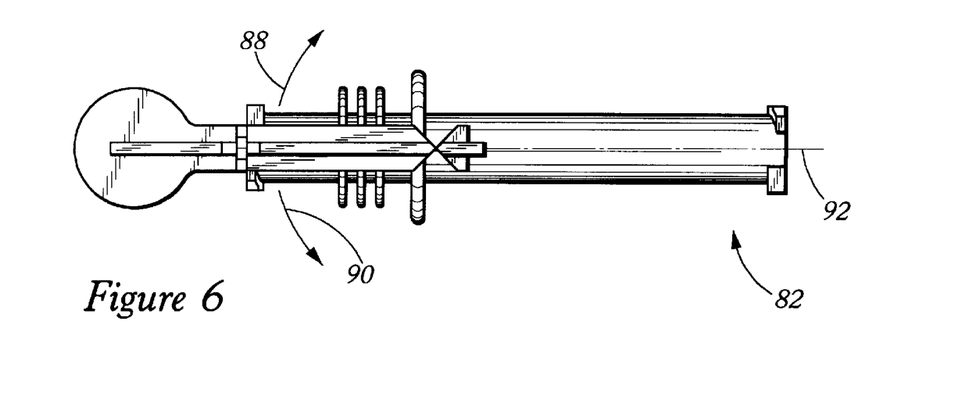
FIG. 6 is a plan view of the third preferred embodiment of the present invention showing the directions in which the cap and cap tether may be rotated.
Figure 7:
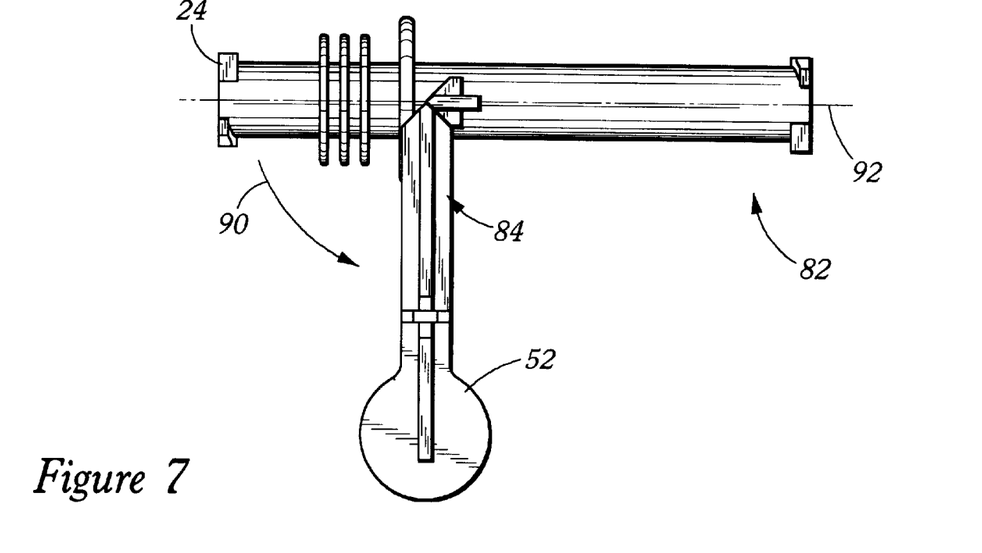
FIG. 7 is a plan view of the third preferred embodiment of the present invention showing the connector cap and cap tether rotated away from the connector's upper open end.

Referring next to FIGS. 5, 6 and 7, a third preferred embodiment 82 of the present invention is shown. The third preferred embodiment 82 is substantially similar to the first preferred embodiment 20, described in FIGS. 1 through 3; except that the cap tether 84 comprises a living hinge 86 that allows the cap tether 84 and cap 52 to pivot in a direction, as denoted by direction arrows 88, 90, perpendicular to the connector body's longitudinal axis 92. FIG. 7 shows the cap tether 84 and cap 52 rotated away from the connector's first open end 24.

Figure 8:
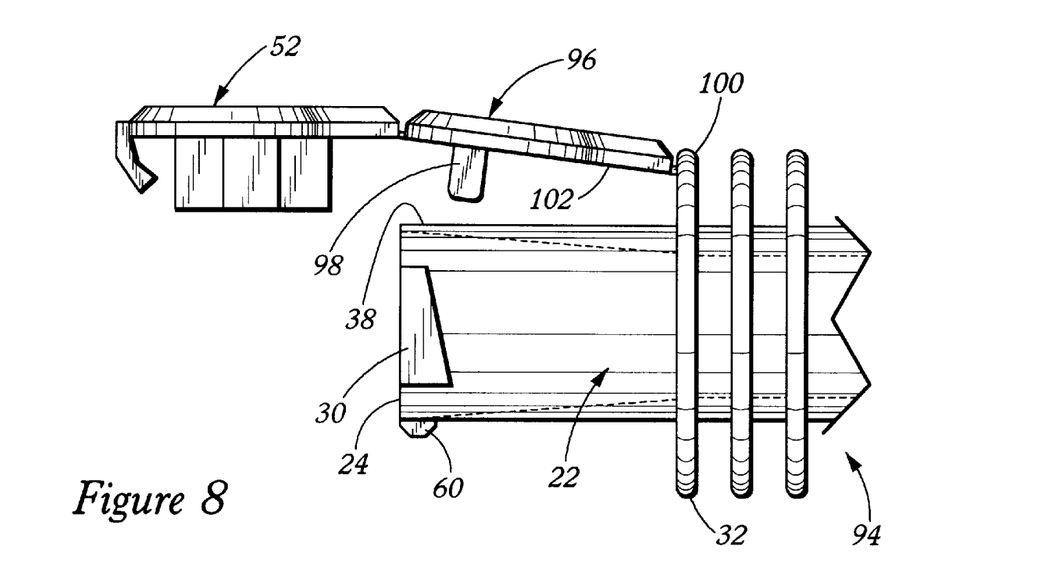
FIG. 8 is a side view of a fourth preferred embodiment of the present invention showing the cap tether pivotally fixed to the top sealing fin of the connector by a living hinge and the cap tether further comprising a pivot stop.
Figure 9:
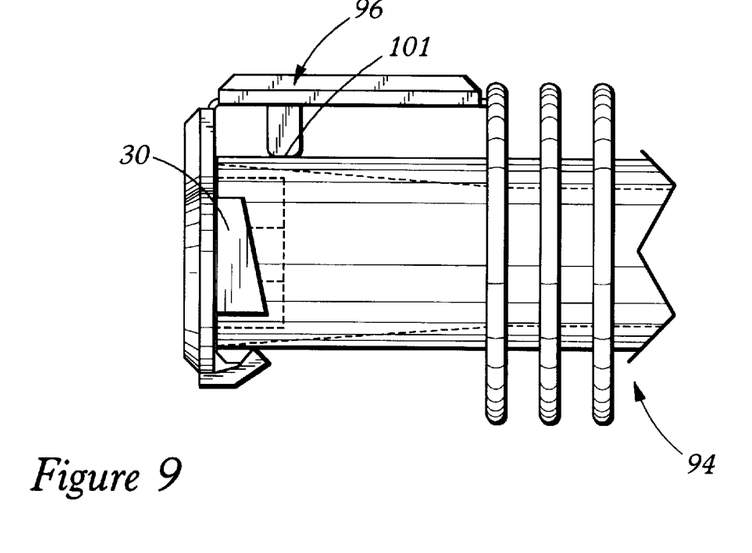
FIG. 9 is a side view of the fourth preferred embodiment of the present invention showing the connector cap in the closed position having the pivot stop contacting the connector body.

Referring next to FIGS. 8 and 9, a fourth preferred embodiment 94 of the present invention is shown. The fourth preferred embodiment 94 of the present invention is substantially similar to the first preferred embodiment 20 except that cap tether 96 comprises a protruding stop 98 and is attached to the connector body's first sealing fin 32 by a hinge 100, preferably a living hinge. The protruding stop 98 may be substantially rectangular and is fixed to the interior surface 102 of the cap tether 96. It is preferred that the cap tether 96 be substantially rigid. During automated capping, the cap tether 96 may be pivoted towards the connector body 22. The protruding stop 98 then contacts the connector's exterior wall 38, holding the hinged cap 52 in the proper orientation to be rotated to the closed position as seen in FIG. 9. The surface 101 of the protruding stop 98 that contacts the tube exterior 38 may be correspondingly curved to fit the convex shape of the tube exterior 38. Cap 52 engages locking protrusion 60.

When the cap 52 is opened, the cap 52 and cap tether 96 may be rotated away from the connector's outer wall 38, removing the protruding stop 98, cap 52 and cap tether 96 from the connector's upper open end 24, thereby allowing a threaded sleeve or the like to engage the connector's thread 30.

Figure 10:
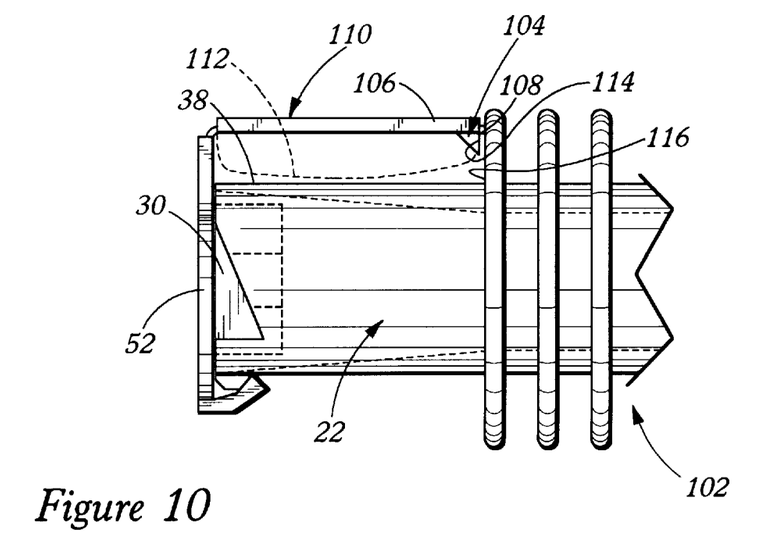
FIG. 10 is a side view of a fifth preferred embodiment of the present invention having a substantially triangular pivot stop disposed at the bottom end of the cap tether and the connector cap in the closed position.

Referring next to FIG. 10, a fifth preferred embodiment 102 of the present invention is shown. The fifth preferred embodiment 102 is substantially similar to the fourth preferred embodiment 94, described in FIGS. 8 and 9, except that the protruding stop 104 comprises a triangular shape and is disposed at cap tether's first end 106. The protruding stop 104 may comprise a triangular shape having a right angle 108. The protruding stop 104 may be fixed to the cap tether's first end 106 having the right angle 108 adjacent to the cap tether 110. Again, it is preferred that the cap tether 110 be substantially rigid; therefore, the cap tether 110 may comprise a reinforcing web 112.

During automated capping, the cap tether 110 is rotated towards the connector body 22 and the bottom leg 114 of the triangular protruding stop 104 contacts the top surface 116 of the connector's first sealing fin 32. When the bottom leg 114 of the triangular protruding stop 104 contacts the sealing fin 32, the rigid cap tether 110 holds the hinged cap 52 in the proper orientation for automated capping. When the cap 52 is opened from the closed position, the cap tether 110 may be rotated away from the connector's exterior wall 38, thereby allowing a threaded sleeve (not shown) to engage the connector's locking protrusion or thread 30.

Figure 11:
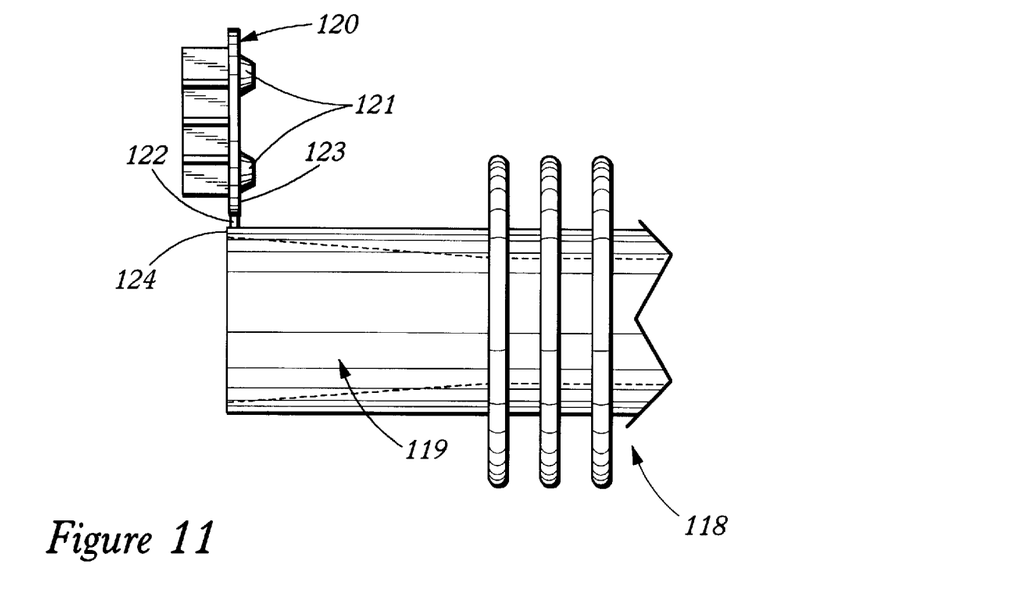
FIG. 11 is a side view of a sixth preferred embodiment of the present invention having a breather cap pivotally fixed to the uppermost outer edge of the connector by a hinge.
Figure 12:
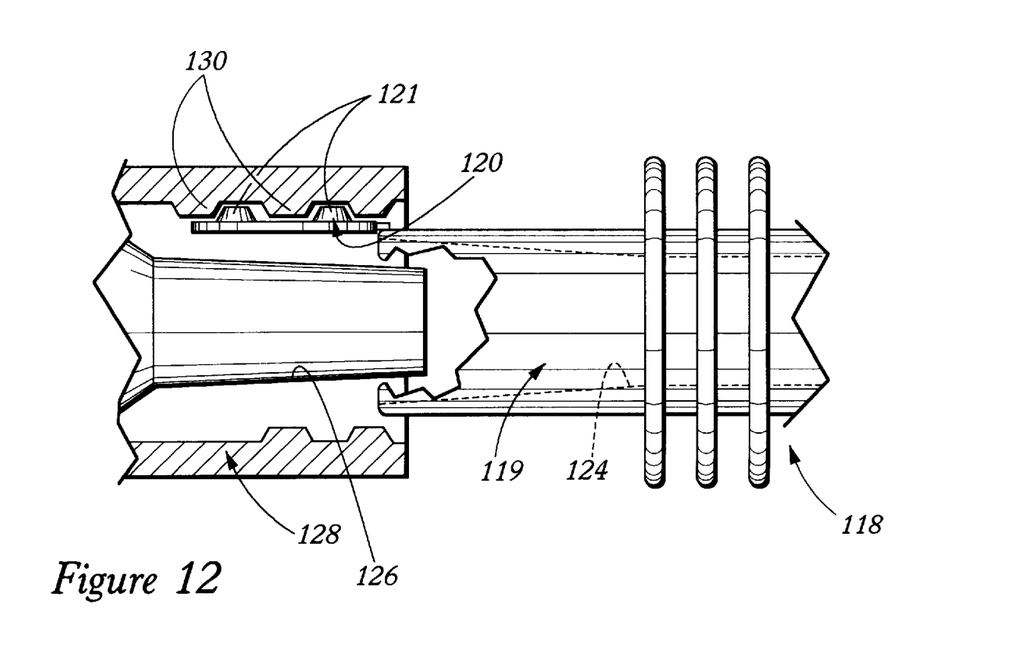
FIG. 12 is a side view of the sixth preferred embodiment of the present invention showing the threads of the breather cap engaging the corresponding grooves of a threaded sleeve of the male luer connector.
Figure 13:
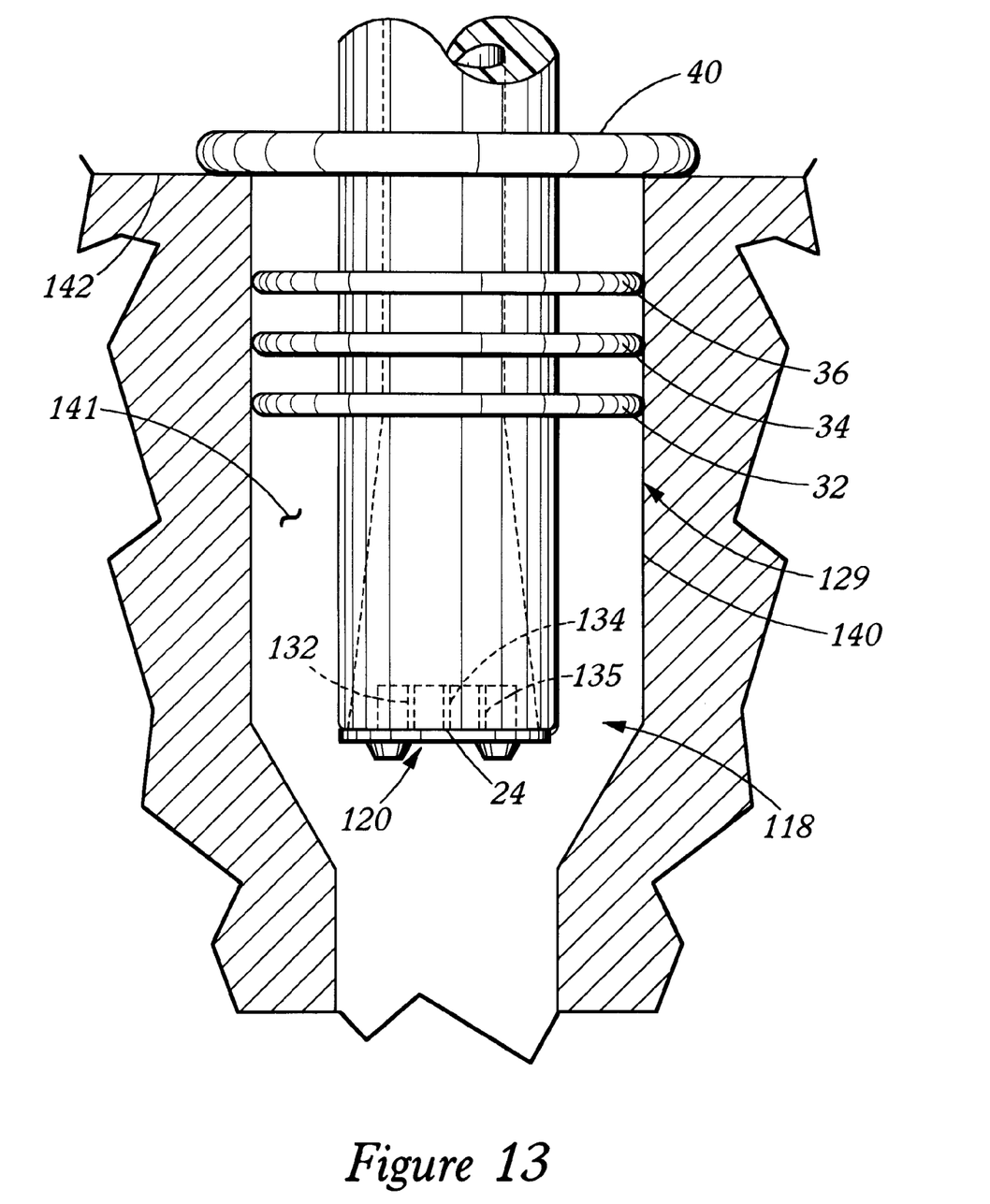
FIG. 13 is a side view of the sixth preferred embodiment of the present invention showing the breather cap in the closed position and the entire capped connector disposed inside a piece of medical equipment.

Referring next to FIGS. 11, 12 and 13, a sixth preferred embodiment of the present invention is shown. The sixth preferred embodiment 118 is substantially similar to the first preferred embodiment 20, described in FIGS. 1 through 3, except that the cap 120 comprises threads 121 on its upper outer surface 123 and is connected to the connector body 119 by a hinge 122 at the connector body's outermost upper edge 124. It is preferred that connecting hinge 122 comprise a living hinge. The hinge 122 may hold the cap 120 in an orientation that facilitates automated capping.

The cap 120 may be positioned parallel to the connector body 119 as seen in FIG. 12. The female luer surface 124 may receive a male tapered surface 126 having a locking sleeve 128. The caps threads 121 may engage the corresponding threads 130 of the locking sleeve 128 to lock the two luer surfaces securely together. The connector 118 may comprise a size sufficiently smaller than standard luer locking devices to allow the cap's threads 121 to engage the threads of a standard size luer locking device's threaded sleeve or the like. Additionally, the connector 118 may comprise a smaller than standard size and the female luer locking surface 124 may comprise a smaller than standard size or circumference allowing a male luer surface to only partially enter the connector 118 while allowing the cap's threads 121 to engage those of the male luer's threaded locking sleeve. The connector 118 may also comprise a standard size while the female luer surface 124 may comprise a smaller size or circumference and the threaded cap 120 may be inset towards the connector's center sufficiently, to allow the threaded cap 120 to engage the threaded sleeve of a standard size luer device.

Alternatively, the cap 120 of the connector 118 may remain closed and the entire connector 118 may be disposed inside a piece of equipment 129 such as the WHO® system of the CENTRY®3 dialysis apparatus. For this application it is preferred that the cap 120 comprise a breather cap to allow fluids to exit the connector 118 through its breather channels 132, 134, 135. In the WHO® system the three sealing fins 32, 34, 36 interfit sealingly with an interior wall 140 of a receptacle 141 provided therefor in the piece of equipment 129. The seating fin 40 abuts a surface 142 of the piece of equipment 129 to position the end 24 of the connector 118 at a desired depth within the receptacle 141. The connector 94 of the fourth preferred embodiment or the connector 102 of the fifth preferred embodiment may also be configured and used in this manner.

Although the present invention has been described with reference to preferred embodiments, numerous modifications and variations can be made and still the result will come within the scope of the invention. No limitation with respect to the specific embodiments disclosed herein is intended or should be inferred.

We claim:

1. A connector for a tubing set comprising:

a hollow tube having an exterior surface;

a cap tether having a first end and a second end, said first end being pivotally attached to the exterior surface of said hollow tube by a first hinge; and a cap pivotally attached to the second end of said cap tether by a second hinge;

whereby said cap tether is substantially rigid.

2. The connector of claim 1, wherein:

said cap tether further comprises an inner surface; and a stop feature fixed to said inner surface of said cap tether.

3. The connector of claim 2, wherein said stop feature further comprises a connecting rib releasably attached to said exterior surface of said hollow tube.

4. The connector of claim 3, wherein:

said connector further comprises a longitudinal axis; and said hinge at said cap tether's first end pivots perpendcularly to said longitudinal axis.

5. The connector of claim 3, wherein:

said hollow tube further comprises an outermost upper edge; and said connecting rib is releasably attached to said outer most upper edge.

6. The connector of claim 2, further comprising at least one luer tapered surface.

7. The connector of claim 6, wherein said cap further comprises a breather cap.

8. The connector of claim 7, wherein:

said hollow tube further comprises a protruding locking lip; and said cap further comprises a hook for engaging said protruding locking lip.

9. A connector according to claim 1 further comprising a connecting rib which is attached to said cap tether and is releasably attached to the exterior surface of said hollow tube.

10. A connector according to claim 9 wherein said cap tether has attached thereto at least one web-like protrusion in communication with said connecting rib.

11. A connector for a tubing set comprising:

a hollow tube having an exterior surface;

a cap tether having a first end and a second end, said first end being pivotally attached to the exterior surface of said hollow tube by a first hinge; and a cap pivotally attached to the second end of said cap tether by a second hinge;

whereby said cap tether is substantially rigid;

wherein said cap tether further comprises an inner surface; and a stop feature fixed to said inner surface of said cap tether;

wherein said stop feature further comprises a connecting rib releasably attached to said exterior surface of said hollow tube; and wherein said cap tether further comprises at least one web-like protrusion in communication with said connecting rib.

12. A connector for a tubing set comprising:

a hollow connector body having an exterior surface and first and second open ends;

a cap tether having first and second ends, said cap tether being substantially rigid yet also having a first and a second thin flexible region, the first thin flexible region being disposed at the first end of said cap tether and the second thin flexible region being disposed at the second end of said cap tether; said first end of said cap tether being pivotally attached to said exterior surface of said connector body such that said first thin flexible region renders said cap tether functionally flexible relative to said connector body; and a cap which is pivotally attached to said second end of said cap tether such that said second thin flexible region renders said cap functionally flexible relative to said cap tether, and said cap being adapted to engage said first open end of said connector body to close said connector.

13. A connector according to claim 12 in which said connector body, said cap tether and said cap are simultaneously molded as a single integral connector.

14. A connector according to claim 13 in which said cap is automatically machine pivoted to engage said first end of said connector body to close said connector.

15. A connector for a tubing set comprising:
a hollow connector body having an exterior surface and first and second open ends;
a cap tether having first and second ends, said cap tether being substantially rigid yet also having a first and a second thin flexible region the first thin flexible region, being disposed at the first end of said cap tether and the second thin flexible region being disposed at the second end of said cap tether; said first end of said cap tether being pivotally attached to said exterior surface of said connector body such that said first thin flexible region renders said cap tether functionally flexible relative to said connector body; and
a cap which is pivotally attached to said second end of said cap tether such that said second thin flexible region renders said cap functionally flexible relative to said cap tether, and said cap being adapted to engage said first open end of said connector body to close said connector; said connector further comprising a breakable connecting rib which is simultaneously attached to said cap tether and to said exterior surface of said connector body by a thin breakable point of weakness.

16. A connector according to claim 15 which said connecting rib is attached to said exterior surface of said connector body adjacent said first open end of said connector body.

17. A connector according to claim 15 which further comprises a web-like protrusion attached to said cap tether.

18. A connector according to claim 17 in which web-like protrusion is adapted to be engaged by a discrete mating connection device which is matingly connectable to the first open end of said connector body such that pressure exerted on said web-like protrusion by said discrete mating connection device during connection of said discrete mating connection device with said first open end of said connector body causes said thin breakable point of weakness of said connecting rib to break and thereby allow the cap tether to pivot away from the connector body.

19. A connector according to claim 18 in which said mating connection device is an internally threaded male luer connector and the first end of said connector body is an externally threaded female luer.

20. A connector for a tubing set comprising:
a hollow connector body having an exterior surface and first and second open ends;
a cap tether having first and second ends said cap tether being substantially rigid yet also having a first and a second thin flexible region, the first thin flexible region being disposed at the first end of said cap tether and the second thin flexible region being disposed at the second end of said cap tether; said first end of said cap tether being pivotally attached to said exterior surface of said connector body such that said first thin flexible region renders said cap tether functionally flexible relative to said connector body; and
a cap which is pivotally attached to said second end of said cap tether such that said second thin flexible region renders said cap functionally flexible relative to said cap tether, and said cap being adapted to engage said first open end of said connector body to close said connector; said connector further comprising a web-like protrusion attached to said cap tether.

21. A connector according to claim 20 in which said web-like protrusion extends from the cap tether toward the exterior surface of said connector body.

22. A connector for a tubing set comprising:
a hollow connector body having an exterior surface and first and second open ends;
a cap tether having first and second ends, said cap tether being substantially rigid yet also having a first and a second thin flexible region, the first thin flexible region being disposed at the first end of said cap tether and the second thin flexible region being disposed at the second end of said cap tether; said first end of said cap tether being pivotally attached to said exterior surface of said connector body such that said first thin flexible region renders said cap tether functionally flexible relative to said connector body; and
a cap which is pivotally attached to said second end of said cap tether such that said second thin flexible region renders said cap functionally flexible relative to said cap tether, and said cap being adapted to engage said first open end of said connector body to close said connector; said connector further comprising at least one sealing fin connected to the exterior surface of the connector body.

* * * * *